United States Patent [19]
Smith

[11] Patent Number: 5,616,127
[45] Date of Patent: Apr. 1, 1997

[54] EXPANDABLE LIQUID INFUSION DEVICE

[76] Inventor: Kevin Smith, 10949 Scripps Ranch Blvd., San Diego, Calif. 92131

[21] Appl. No.: 340,072

[22] Filed: Nov. 14, 1994

[51] Int. Cl.[6] .................................................. A61M 37/00
[52] U.S. Cl. ............................................. 604/118; 604/132
[58] Field of Search ................................... 604/132, 133, 604/140, 141, 145, 153, 118

[56] References Cited

U.S. PATENT DOCUMENTS

| | | | |
|---|---|---|---|
| 4,379,453 | 4/1983 | Baron | 604/145 |
| 4,443,218 | 4/1984 | DeCant et al. | 604/67 |
| 5,059,182 | 10/1991 | Laing | 604/141 |
| 5,090,963 | 2/1992 | Gross et al. | 604/145 |
| 5,163,920 | 11/1992 | Olive | 604/141 |
| 5,318,540 | 6/1994 | Athayde et al. | 604/153 |
| 5,368,571 | 11/1994 | Horres | 604/131 |

*Primary Examiner*—Todd E. Manahan
*Attorney, Agent, or Firm*—Gilliam, Duncan & Harms

[57] ABSTRACT

This invention is directed to a temperature activated infusion device for delivering a specific quantity of medication to a recipient patent. The delivery is accomplished by the use of a sealed pouch or container of an temperature expandable fluid which applies pressure to a adjacent second pouch or container of liquid medication. A medication delivery pressure regulator and fluid metering valve associated with the output of the liquid medication from the pouch or container insure proper pressure and volume of medication to the recipient patient.

23 Claims, 2 Drawing Sheets

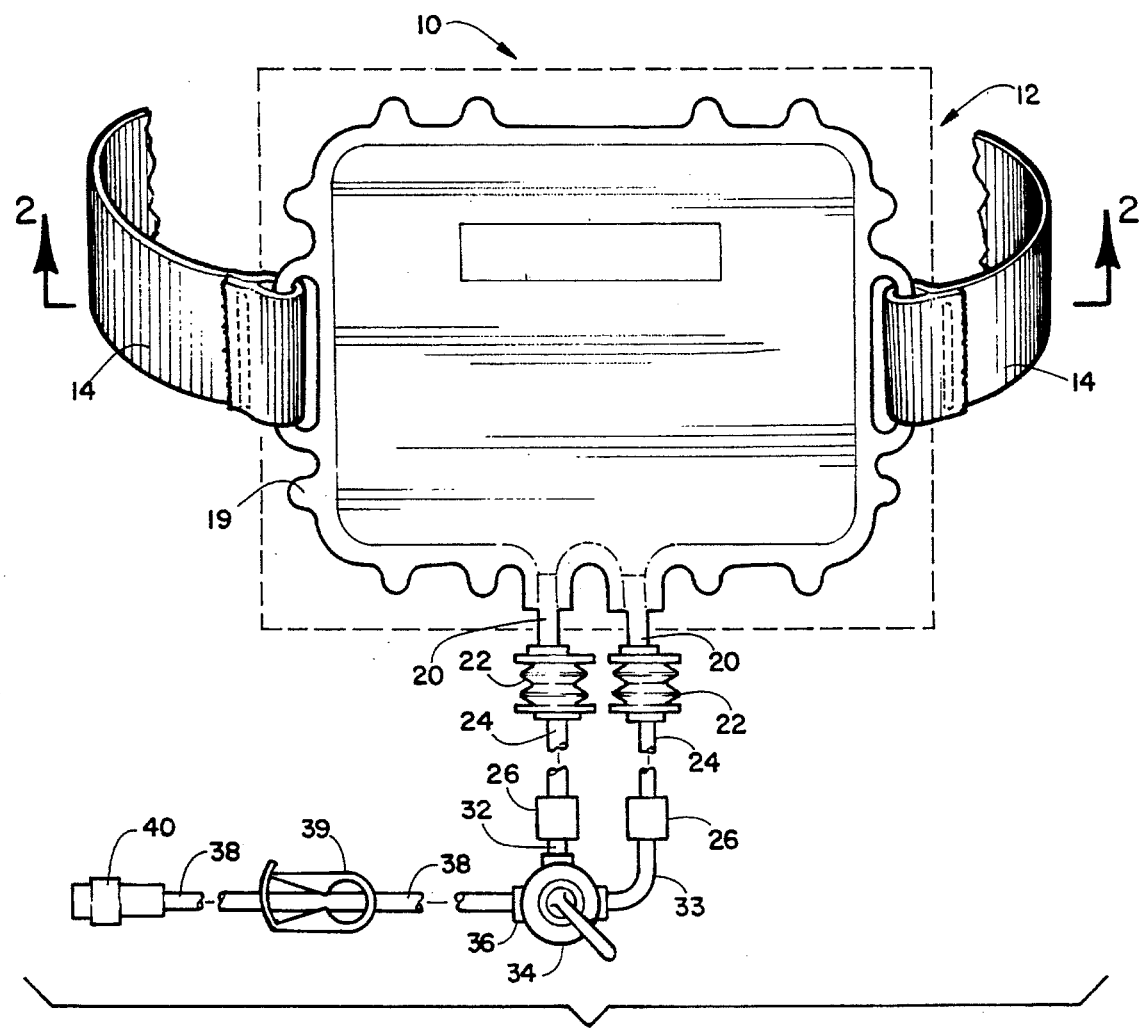
FIGURE 1
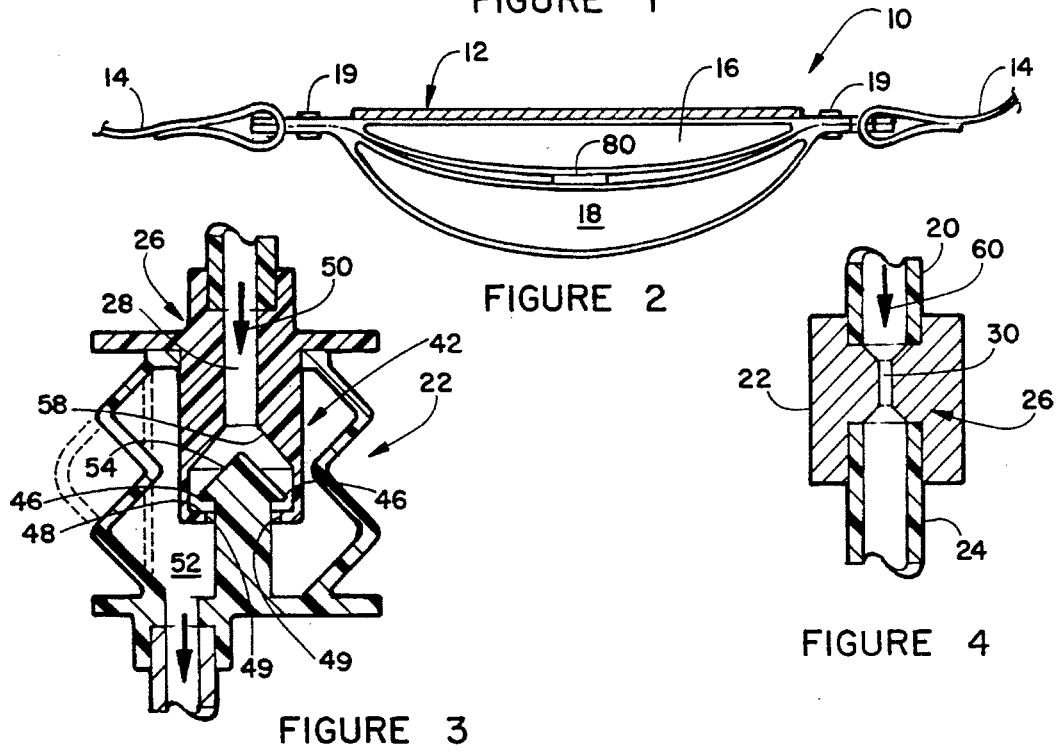
FIGURE 2
FIGURE 3
FIGURE 4

EXPANDABLE LIQUID INFUSION DEVICE

This invention is directed to a medication infusion device and more particularly to a medication infusion device that is operated by a sealed container of temperature expansive fluid pressing against an adjacent flexible container of medication and applying pressure to the medication contents of that container thereby forcing the medication to infuse from the container to the patient.

There are a plurality of infusion devices presently existing in the medical art. Generally these devices deliver medication to the patient by means of either electrical or mechanical pump as the driving force. These devices are generally constructed of complicated electrical or mechanical pumps with many working parts and therefore are susceptible to malfunction or breakdown which can result in the failure of the pump to deliver necessary medication to the patient resulting in more serious illness or possible death.

Another common method of delivering liquid medication to a patient is by the use of gas under pressure. Examples of these devices can be found in the following U.S. Pat. No. , 4,857,055 by Paul Y. Wang; U.S. Pat. No. 5,151,093 by Felix Theeuwes et al.; U.S. Pat. No. 5,167,633 by Alfred E. Mann et al.; U.S. Pat. No. 5,167,625 by Stephen et al.; and U.S. Pat. No. 5,242,406 by Joseph Gross et al..

Of the prior art devices only U.S. Pat. No. 5,167,633 utilizes a sealed container of an expandable fluid for applying a constant below atmosphere pressure to a container of medication. This patent teaches only that pressure is applied to the medication container to make liquid available to the pump and maintaining that pressure below atmospheric pressure. The pressure from the container of expandable fluid is not used to deliver the medication to the patient. A medication infusion pump is used for this purpose. A pressure below that of atmospheric pressure is insufficient pressure for delivering medication to the patient.

There has not been a simple, inexpensive, noncomplex method of delivering medication to a patient at a selected constant volume at a selected pressure without the use of an infusion pump per se or gas pressure until the emergence of the instant invention.

SUMMARY OF THE INVENTION

Applicant's invention is directed to the delivery of medication to a recipient patient without the need of expensive and complex pump or gas delivery means.

A pouch constructed of either inflexible or slightly expandable material contains a sealed expandable first container filed with a temperature expandable fluid such as, by way of example and not by way of limitation, Acetaldehyde, Cyclobutane, 22Dimethypropane or EthyleneAmine and a second flexible container containing a liquid medication to be infused into a patient. A regulator and a pressure control associated with the liquid medication output from the second container controls the pressure and volume of the liquid medication entering the patient. When the pouch is constructed of a slightly expandable material the pouch material is less expandable than the material of the first flexible container so that when the first sealed container reaches a selected internal pressure the pouch expands slightly to relieve some of the pressure applied to the second container to maintain a regulated flow of liquid medication from the second container.

In operation ambient or patient body temperature causes the expandable fluid in the first container to expand and apply dispensing pressure to the second flexible container of medication fluid. The pressure applied to the second container causes the liquid to be forced from the second container through a delivery tube into a pressure regulator, thorough a volume regulator and then through a syringe, needle or the like into the recipient patent.

Several embodiments of pressure regulators are used. One embodiment comprises a bellows type valve means that reduces regulator output pressure as the bellows expands form increased medication pressure. A second embodiment utilizes an open cell foam material with continuous open cells disposed between the first expandable container and the flexible second liquid medication container which causes the open cells to begin to close varying degrees directly related to a relative pressure increase between the two containers thereby reducing flow through the open cell foam until such elevated pressure causes the flow to terminate until the pressure thereon is reduced.

The volume of liquid medication is controlled by at least one metering orifice. At least three different fluid medication volummes leaving the device prior to entering the recipient patient can be selected by the use of a three way valve and two metering orifices.

The first and second containers are generally attached together around their periphery in a manner that transfers the pressure developed in the first container to the second container for forcing the contents therefrom through a tube extending from the inside thereof. The two containers are contained within a fanny pack type pouch attached to the patient's by a belt or the like in a conventional manner.

An object of this invention is to produce a medication diffusion device which does not require an infusion pump per se.

Another object of this invention is to provide a medication infusion device which delivers medication liquid under pressure developed only by abient or patient temperature.

Still another object of this invention is to produce a medication infusion device utilizing a pressure regulator controlled by the pressure developed by expansion of an expandable fluid.

Yet another object of this invention is to produce a pressure regulator positioned between a first container containing an expandable fluid and a second container containing the medication to be infused into the recipient patient that regulates flow therethrough.

Still another object of this invention is to regulate the pressure applied to a second container containing a infusion liquid by a first sealed container containing an expandable fluid by providing a pouch for containing the two containers that is constructed of slightly flexible material that os less flexible than the material of construction of the first container to prevent overpressurizing the contents of the second container.

These and other objects and advantages of the present invention will become apparent to those skilled in the art after considering the following detailed specification in which the preferred embodiment are described in conjunction with the accompanying drawing Figures.

BRIEF DESCRIPTION OF THE DRAWINGS

FIG. 1 is a side elevation showing of the infusion device of this invention;

FIG. 2 is a section taken along line 2—2 of FIG. 1;

FIG. 3 is a side cutaway showing of a first embodiment of a pressure metering valve;

FIG. 4 is a side cutaway showing a volume metering orifice;

DETAILED DESCRIPTION OF THE PREFERRED EMBODIMENT

Figure 5:
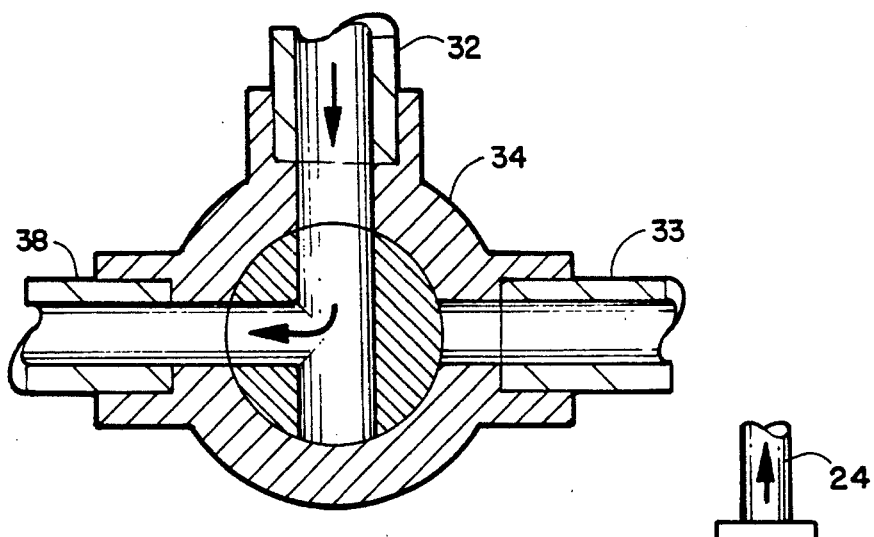
FIG. 5 is a cutaway showing of a three way control valve.

Referring now to the various drawing Figures which depict the medication infusion device 10 of the present invention. Referring now specifically to drawing FIGS. 1 and 2. A pouch 12, shown as cut away exposing the contents therein, such as a "fanny pack", as for example and not by way of limitation, with a belt 14 for securing the pouch to a person receiving liquid medication from the device of the invention. The pouch is constructed from material that is slightly expendable or nonexpendable, that is it either stretches slightly or does not stretch when internal pressure is applied to the walls thereof. Such material can be Nylon or the like suitable for the purpose intended.

Referring now to drawing FIG. 2, the pouch 12 contains a pair of expandable (resilient) first and second containers 16 and 18 respectively. The containers 16 and 18 are secured together around their periphery by means of fusion welds, rivets, bolts or the like so that as the container 16 expands, as hereinafter explained in detail, the pressure of expansion of container 16 will be applied directly to the container 18 and the medication liquid contained therein deforming the container 18 inwardly thereby applying pressure to the contents of container 18 while the pouch 12 maintains substantially its original form. When the pouch 12 is constructed of slightly flexible or stretchable material any excess pressure build up in container 16 is relieved a selected amount by the stretching of the pouch thereby preventing over pressurizing of the contents of pouch 18.

Container 16 is filled with an expandable fluid such as, by way of example and not by of limitation, Acetaldehyde, Cyclobutane, 22Dimethypropane or EthyleneAmine and container 18 contains a liquid medication to be infused into a patient. Preferably, the fluid in the first container will expand and apply pressure in the temperature range of from 65 to 100 degrees F. However, it may be necessary to select expandable fluids beyond the limits of the preferable range of temperature.

At least one tube 20 extends from the inner portion of container 18 allowing the medication liquid under pressure to exit the container 18 into the tube 20. Two tubes 20 are shown for providing a selective volume of medication liquid from the container 18 to the recipient patient.

The tube or tubes 20 extend to a pressure metering valve 22 in the form of a bellows regulator herein after described in more detail.

Tube or tubes 24 exit the pressure metering valve or valves 22 and connect to series metering orifices 26. The metering orifices 28 and 30 are shown in more detail in drawing FIGS. 3 and 4.

The output from the metering orifices are connected in series through tubes 32 and 33 to a three way metering valve 34. A more detailed showing of the three way valve 34 is shown in drawing FIG. 5 and hereinafter explained in more detail.

The output 36 of the metering valve 34 is connected through a tube 38 to a manual flow stop valve 39 and then to syringe or needle connection 40. The syringe or needle, not shown, is then inserted into the recipient patient, not shown, for medication infusion.

Referring now specifically to drawing FIG. 3, pressure metering valve 22 includes a built in combination metering restriction 28 and a bellows activated pressure limiting valve 42. As the pressure increases within the valve 22 the walls 44 of the bellows expand, as shown in phantom, forcing protrusion 46 upward in the Figure toward the top of the drawing and seating against the inner surface 58 of the valve. When the desired flow pressure through the limiting valve 42 is exceeded the tip 54 seats against inner surface 58 and the flow through aperture 49 along arrows 50 and 52 through the valve 42 is terminated. In the absence of any pressure within the valve 22, the tip 54 of member 56 attached to the bellows is biased by the bellows toward orifice seat 48 at the lower distal end of the valve 28. Fluid from container 18 is allowed to flow normally through aperture 49 when protrusions 46 and tip 54 are intermediate extensions 48 and orifice seat 58 as shown in the drawing FIG. 3.

Referring now to drawing FIG. 4, a metering orifice 26 is shown with flow restriction 30 intermediate the input and output of tubes 20 and 24 respectively. The diameter of the restriction 30 determines the volume of the flow in the direction of arrow 60.

Referring now to drawing FIG. 5 which depicts a three way valve 34. Tube 32 delivers one half of the volume of tube 33 to the valve 34, therefore, the valve in the position shown delivers a first volume of liquid medication, when the valve is rotated counterclockwise 90 degrees the valve delivers a second volume of liquid medication equal to twice the first volume and when rotated clockwise 90 degrees from the position shown in drawing FIG. 5 the valve delivers the sum of the first and second volummes. When rotated 180 degrees from the position shown in drawing FIG. 5, the valve is closed to any flow. The valve 34 can be manually operated as shown in FIG. 1 or motor driven and operated by time/sequence.

Figure 6:
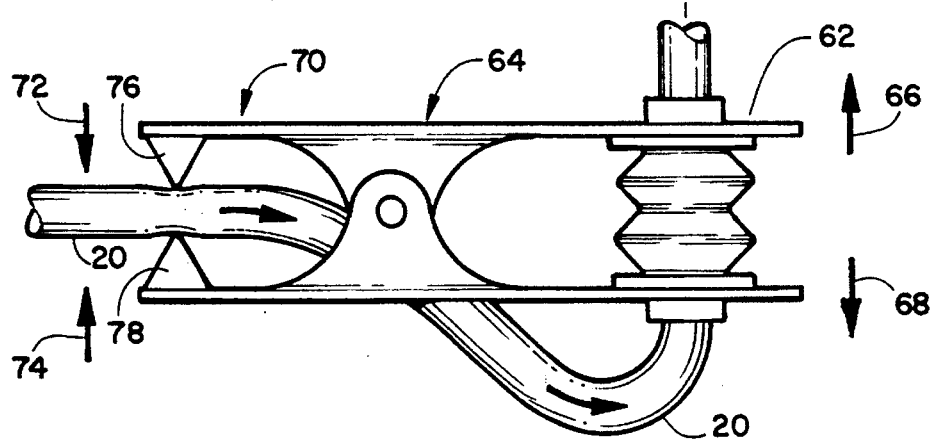
FIG. 6 is a cutaway showing of a pressure controlled volume regulation valve.

Referring now to drawing FIG. 6, which depicts a second volume flow control to prevent excessive line pressure. It can be easily understood that as the bellows expands due to internal pressure, as hereinbefore discussed, one end 62 of a clamp pivotable at pivot 64 spreads apart between arrows 66 and 68 causing clamp end 70 move together between arrows 72 and 74 squeezing tube 20 between extensions 76 and 78 shutting off or at least limiting the flow of liquid medication through tube 20. The bellow walls hold the extensions 76 and 78 apart when low or no pressure is present internal of the bellows walls.

Figure 7:
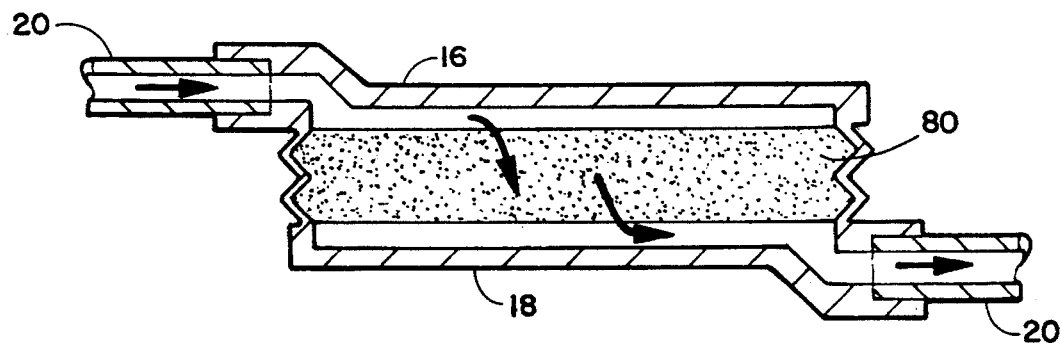
FIG. 7 is a partial cutaway showing of a second embodiment of a volume pressured controlled volume regulation valve.

Referring now to drawing FIGS. 1 and 7. Drawing FIG. 7 depicts a cutaway showing of a section of drawing FIG. 1 depicting a pressure control valve formed from resilient open cell foam material 80 disposed between the first and second containers. The cells of the foam allow the liquid medication to flow therethrough in a volume depending upon the pressure exerted upon the container 18 by the fluid expanding in container 16, i.e. the greater the pressure exerted upon container 18 by container 16 the less the volume of fluid medication flow through the foam. The compression of the foam restricts the flow through the open cells.

In operation, the sealed container 16 containing temperature expandable fluid is physical connected to container 18 containing a liquid medication to be delivered to a recipient patient at a controlled volume and pressure. The connection of the two containers together causes the pressure built up in container 16 to be applied to container 18 effectively pressuring the contents of container 18 causing the liquid medication in the container to commence to flow from tube 20 to one of the pressure regulators, through a volume metering orifice which limits the flow from the orifice. The output of the metering orifice is valved to insure the desired volume delivered to the patient.

The containers 16 and 18 can be removably attached or fixedly attached to each other.

The pressure developed by the fluid in container 16 is greater than that pressure required to deliver the liquid medication to the recipient patient at a normal ambient range of temperatures at a selected range of altitudes or atmospheric pressures.

In some uses it may be beneficial to add a heat transfer medium conductive plate 82 formed of heat conductive material such, as for example, metal, metallic material or the like as the inner wall of the pouch 12, see drawing FIG. 2, which is positioned normally adjacent to or next to the body of the liquid medication recipient patent. The heat transfer medium 82 could be positioned directly against the skin of the patient or against a garment worn by the patient.

While specific embodiments of the method and apparatus for the liquid medication delivery device of the present invention has been shown and fully explained above for the purpose of illustration it should be understood that many alterations, modifications and substitutions may be made to the instant invention disclosure without departing from the spirit and scope of the invention as defined by the appended claims.

What is claimed is:

1. A temperature activated medication infusion pump attachable to an infused medication recipient comprising:

means for attaching said infusion pump to said a patient;

a first container having a central hollow portion containing a temperature expandable fluid, said expandable fluid being expandable through a selected range of temperatures;

a second container having a hollow central portion containing a liquid medication;

means for attaching said first container to said second container, whereby when said first container expands pressure is applied to said second container and the liquid medication therein;

a tube communicating with the hollow portion of said second container with a distal end extending therefrom;

a pressure control means associated with said second container for controlling the pressure of said liquid medication flowing from said second container through said tube, said pressure control means connected to the distal end of said tube;

valve means for metering the volume of said liquid medication flowing through said tube; and means for attaching a device for infusing said liquid mediation from said tube into said patent.

2. The invention as defined in claim 1 wherein said means for attaching said infusion pump to said recipient comprises a pouch for containing said first and second containers attachable to said patient by a belt.

3. The invention as defined in claim 2 wherein at least one surface of said pouch adjacent to said first container is formed of a heat transfer medium.

4. The invention as defined in claim 3 wherein said heat transfer medium is metal.

5. The invention as defined in claim 2 wherein said first and second containers are fixedly secured to each other around their outer peripheries.

6. The invention as defined in claim 2 wherein said first and second containers are removably secured to each other around their outer peripheries.

7. The invention as defined in claim 1 wherein said pouch is constructed of a material substantially inflexible.

8. The invention as defined in claim 1 wherein said first and second containers are fabricated from a flexible material.

9. The invention as defined in claim 8 wherein said flexible material is plastic.

10. The invention as defined in claim 1 wherein said range of temperatures is from 65 to 100 degrees F.

11. The invention as defined in claim 1 wherein said expandable fluid consists of one of the following Acetakdehyde, Cyclobutane, 22Dimethylpropane or EthyleneAmine.

12. The invention as defined in claim 1 wherein said pressure control means is a pressure regulator.

13. The invention as defined in claim 1 wherein said pressure control means is resilient open cell foam inserted between said first and second container in series between said hollow portion of said second container and said tube whereby as the pressure increases in said first container relative to said second container said flow through said tube is reduced by compressing said foam thereby.

14. The invention as defined in claim 1 wherein said hollow portion of said first container is sealed.

15. The invention as defined in claim 1 wherein said valve means comprises a plurality of different volume settings.

16. The invention as defined in claim 1 wherein said volume control means comprises at least three different volume settings.

17. The invention as defined in claim 1 wherein said pressure control means comprises a bellows actuated flow control whereby as the pressure in the hollow portion of said first container increases said flow to said means for infusing said liquid decreases.

18. The invention as defined in claim 1 wherein at least one surface of said pouch adjacent of said first container is metallic.

19. The invention as defined in claim 1 wherein said valve means is manually operated.

20. A temperature activated medication infusion pump comprising:

a first container having a central hollow portion containing a temperature expandable fluid, said expandable fluid being expandable through a selected range of temperatures;

a second container having a hollow central portion containing a liquid medication;

means for attaching said first container to said second container, whereby when said first container expands pressure is applied to said second container and the liquid medication therein;

a tube communicating with the hollow portion of said second container with a distal end extending therefrom;

pressure control means for controlling the pressure of said liquid medication flowing from said second container through said tube;

means for metering the volume of said liquid medication flowing through said tube; and means for attaching a device for infusing said liquid mediation from said tube into said patent.

21. A temperature activated medication infusion pump comprising:

a first container having a central hollow portion containing a temperature expandable fluid, said expandable fluid being expandable through a selected range of temperatures;

a second container having a hollow central portion containing a liquid medication;

means for attaching said first container to said second container, whereby when said first container expands pressure is applied to said second container and the liquid medication therein;

a tube communicating with the hollow portion of said second container with a distal end extending therefrom;

means for metering the volume of said liquid medication flowing through said tube; and means for attaching a device for infusing said liquid mediation from said tube into said patent.

22. A temperature activated medication infusion pump comprising:

a first container having a central hollow portion containing a temperature expandable fluid, said expandable fluid being expandable through a selected range of temperatures;

a second container having a hollow central portion containing a liquid medication;

means for attaching said first container to said second container, whereby when said first container expands pressure is applied to said second container and the liquid medication therein;

a tube communicating with the hollow portion of said second container with a distal end extending therefrom; and means for attaching a device for infusing said liquid mediation from said tube into said patent.

23. A temperature activated medication infusion pump comprising:

a first container having a central hollow portion containing a temperature expandable fluid, said expandable fluid being expandable through a selected range of temperatures;

a second container having a hollow central portion containing a liquid medication; and a tube communicating with the hollow portion of said second container with a distal end extending therefrom, whereby when said first container expands pressure is applied to said second container and the liquid medication therein forcing liquid medication from said tube.

* * * * *